United States Patent [19]
Wallace et al.

[11] Patent Number: 6,126,733
[45] Date of Patent: Oct. 3, 2000

[54] ALCOHOL BASED PRECURSORS FOR PRODUCING NANOPOROUS SILICA THIN FILMS

[75] Inventors: Stephen Wallace, Albuquerque, N. Mex.; James Drage, Fremont, Calif.; Teresa Ramos; Douglas M. Smith, both of Albuquerque, N. Mex.

[73] Assignee: AlliedSignal Inc., Morristown, N.J.

[21] Appl. No.: 09/111,081

[22] Filed: Jul. 7, 1998

Related U.S. Application Data

[60] Provisional application No. 60/063,815, Oct. 31, 1997.

[51] Int. Cl.$^7$ ................................................. C09D 103/00
[52] U.S. Cl. ............................... 106/287.16; 106/287.14; 427/96; 428/447; 438/780; 438/790
[58] Field of Search ........................ 106/287.14, 287.16; 427/96; 428/447; 438/780, 790

[56] References Cited

U.S. PATENT DOCUMENTS

| | | | |
|---|---|---|---|
| 4,865,649 | 9/1989 | Kashwagi et al. | 106/287.16 |
| 5,504,042 | 4/1996 | Cho et al. | 437/247 |
| 5,514,211 | 5/1996 | Marks et al. | 106/287.16 |
| 5,736,425 | 4/1998 | Smith et al. | 438/778 |
| 5,795,378 | 8/1998 | Sakamoto et al. | 106/287.16 |

FOREIGN PATENT DOCUMENTS

| | | |
|---|---|---|
| 0459003 | 4/1991 | European Pat. Off. . |
| 0776925 | 4/1997 | European Pat. Off. . |
| 0775669 | 5/1997 | European Pat. Off. . |

*Primary Examiner*—David Brunsman
*Attorney, Agent, or Firm*—Leslie A. Weise

[57] ABSTRACT

The invention relates to nanoporous dielectric films and to a process for their manufacture. Such films are useful in the production of integrated circuits. Such films are produced from a precursor of an alkoxysilane; a relatively low volatility solvent composition comprising a e $C_1$ to $C_4$ alkylether of a $C_1$ to $C_4$ alkylene glycol which is miscible in water and alkoxysilanes, having a hydroxyl concentration of 0.0084 mole/cm$^3$ or less, a boiling point of about 175° C. or more at atmospheric pressure and a weight average molecular weight of about 120 or more; a relatively high volatility solvent composition having a boiling point below that of the relatively low volatility solvent composition; optional water and an optional catalytic amount of an acid.

41 Claims, 4 Drawing Sheets

ALCOHOL BASED PRECURSORS FOR PRODUCING NANOPOROUS SILICA THIN FILMS

CROSS REFERENCE TO RELATED APPLICATION

This application claims the benefit of provisional application Ser. No. 60/063,815 filed Oct. 31, 1997 which is incorporated herein by reference.

BACKGROUND OF THE INVENTION

1. Field of the Invention

The present invention relates to nanoporous dielectric films and to a process for their manufacture. Such films are useful in the production of integrated circuits.

2. Description of the Prior Art

As feature sizes in the production of integrated circuits approach 0.25 μm and below, problems with interconnect RC delay, power consumption and crosstalk all become more significant. Integration of low dielectric constant materials for interlevel dielectric (ILD) and intermetal dielectric (IMD) applications partially mitigate these problems, however each of the material candidates having K significantly lower than dense silica suffer from disadvantages. A number of organic and inorganic polymers have K in the range of 2.2 to 3.5, however, these polymers suffer from problems including low thermal stability, poor mechanical properties including low glass transition temperature (Tg), sample outgassing, and long term reliability questions. One alternative is to employ nanoporous silicas which can have dielectric constants in the range of about 1 to 3. Nanoporous silica is attractive because it employs similar precursors (e.g., TEOS, tetraethoxysilane) as used for spin-on glasses (SOG's) and CVD $SiO_2$ and because of the ability to control pore size of the nanoporous silica. In addition to low dielectric constant, nanoporous silica offers other advantages for microelectronics including thermal stability up to 900° C., small pore size (<<microelectronics features), use of materials that are widely used in the semiconductor industry namely silica and precursors (e.g., TEOS), the ability to tune dielectric constant over a wide range, and deposition using similar tools as employed for conventional SOG processing.

Nanoporous silica films can be fabricated by using a mixture of a solvent composition and a silica precursor which is deposited onto a wafer by conventional methods of spincoating, dip-coating, etc. The silica precursor is polymerized by chemical and/or thermal means until it forms a gel. Film thickness and density/dielectric constant can be controlled independently by using a mixture of two solvents with significantly different volatility. The more volatile solvent evaporates during and immediately after precursor deposition. The second solvent is then removed by increasing the temperature. EP patent application EP 0 775 669 A2, which is incorporated herein by reference, shows a method for producing a nanoporous silica film with uniform density throughout the film thickness.

Nanoporous silicas are preferably prepared from precursors comprising an alkoxysilane, a relatively high volatility solvent and a relatively low volatility solvent which is a polyol having an ether linkage. The principal reactions for an alkoxysilane such as tetraethoxysilane, tetramethoxysilane, triethoxysilane, methyltriethoxysilane, colloidal silica, and silica precursors which contain silicon-organic-silicon linkages are shown below. The following are exemplary reactions since the extent of hydrolysis and transesterification can vary from 0 to 4.

1) Hydrolysis: $Si(OR)_4 + H_2O \leftrightarrow Si(OR)_3OH + ROH$
2) Transesterification: $Si(OR)_4 + R"OH \leftrightarrow Si(OR)_3OR" + ROH$
3) Water condensation: $Si(OR)_3OH + Si(OR)_3OH \leftrightarrow Si(OR)_3OSi(OR)_3 + H_2O$
4) Alcohol condensation: $Si(OR)_3OH + Si(OR)_4 \leftrightarrow Si(OR)_3OSi(OR)_3 + ROH$ Thus, to completely hydrolyze and condense a tetrafunctional alkoxysilane such as TEOS, two moles of water are required per mole of silane. Typically, the precursor is prepared with an insufficient quantity of water so that stability is maintained during transportation and storage. After deposition, additional water is absorbed into the film and reactions may go to the desired completion. The problem is that the surface chemistry and molecular weight of the precursor changes dramatically during deposition and post-processing. During the initial deposition, the silicon polymer is primarily covered with alkoxy groups which are immiscible with water. At the same time, the composition of the solvent system is changing dramatically as the high volatility solvent (typically, an alcohol such as ethanol or isopropanol) rapidly evaporates during deposition. During the initial deposition, the silicon precursor polymer is primarily covered with alkoxy groups which are immiscible with water. However, after exposure to additional water and a catalyst, the surface rapidly changes to a hydrophilic surface primarily covered with silanol groups (SiOH). In order to avoid the possibility of microphase separation in the gel which can result in the presence of defects in the film and film appearance problems such as hazing and streaks, we have recently discovered that the low volatility pore control solvent (PCS) must have a set of properties which were not heretofore known.

It has now been found that the low volatility polyol solvent must meet a number of criteria which were previously not known in order to achieve a stable precursor solution. In addition to having a high boiling point and proper solubility in water and alkoxysilanes, important criteria are low hydroxyl concentration and high molecular weight. In order to obtain films of high quality, i.e. having no defects, no large pores, etc., it has been discovered that the silane precursor and water should be miscible in the pore control solvent. During precursor synthesis, the components are typically made mutually miscible via the high volatility solvent. However, this invention is predicated on these components being miscible in the PCS after the high volatility solvent has evaporated. In order to obtain precursor solutions which are stable over long time (i.e. months) and which will give nanoporous silica films with desirable properties such as high surface area, high mechanical strength, and small pore size, the solvents need to be employed with volumetric hydroxyl concentrations in the correct range. The desired range of hydroxyl concentration depends upon the target dielectric constant.

According to the invention one group of solvents that are uniquely suited to meeting each of these constraints are the monomethyl ethers of ethylene glycol and propylene glycol. The compounds have ether linkages (C—O—C) and alcohol groups (COH). A single compound may be used or a mixture of compounds may be employed to achieve the desired properties. When a pore control solvent is used which does not exhibit adequate miscibility with both the alkoxysilane and water, defects in the film are observed. Scanning electron micrographs of nanoporous silica films produced using either a PCS (e.g., tetraethylene glycol) which has appropriate properties such as boiling point and hydroxyl content but which is not miscible with TEOS and made using a PCS (e.g., triethylene glycol monomethyl ether), which is the subject of this invention and which is miscible with both TEOS and water, demonstrate that the defects which can arise as a result of miscibility problems are readily apparent for the film made with the tetraethylene glycol, but not with the film made with the triethylene glycol monomethyl ether.

SUMMARY OF THE INVENTION

The invention provides a nanoporous silica precursor composition which comprises at least one alkoxysilane; at least one relatively low volatility solvent composition comprising a linear or branched $C_1$ to $C_4$ alkyl ether of a $C_1$ to $C_4$ alkylene glycol which is miscible in water and alkoxysilanes, having a hydroxyl concentration of 0.0084 mole/cm$^3$ or less, a boiling point of about 175° C. or more at atmospheric pressure and a weight average molecular weight of about 120 or more; at least one relatively high volatility solvent composition having a boiling point below that of the relatively low volatility solvent composition; optional water and an optional catalytic amount of an acid.

The invention further provides a process for forming a nanoporous dielectric coating on a substrate which comprises a) blending a nanoporous silica precursor composition which comprises at least one alkoxysilane; at least one relatively low volatility solvent composition comprising a linear or branched $C_1$ to $C_4$ alkyl ether of a $C_1$ to $C_4$ alkylene glycol which is miscible in water and alkoxysilanes, having a hydroxyl concentration of 0.0084 mole/cm$^3$ or less, a boiling point of about 175° C. or more at atmospheric pressure and a weight average molecular weight of about 120 or more; at least one relatively high volatility solvent composition having a boiling point below that of the relatively low volatility solvent composition; optional water and an optional catalytic amount of an acid, thus forming a mixture and causing a partial hydrolysis and partial condensation of the alkoxysilane;

b) depositing the composition onto a substrate while evaporating at least a portion of the relatively high volatility solvent composition;

c) exposing the composition to a water vapor and a base vapor; and d) evaporating the relatively low volatility solvent composition, thereby forming a relatively high porosity, low dielectric constant, silicon containing polymer composition on the substrate.

The invention also provides a semiconductor device produced by the process which comprises:

a) blending a nanoporous silica precursor composition which comprises at least one alkoxysilane; at least one relatively low volatility solvent composition comprising a linear or branched $C_1$ to $C_4$ alkyl ether of a $C_1$ to $C_4$ alkylene glycol which is miscible in water and alkoxysilanes, having a hydroxyl concentration of 0.0084 mole/cm$^3$ or less, a boiling point of about 175° C. or more at atmospheric pressure and a weight average molecular weight of about 120 or more; at least one relatively high volatility solvent composition having a boiling point below that of the relatively low volatility solvent composition; optional water and an optional catalytic amount of an acid, thus forming a mixture and causing a partial hydrolysis and partial condensation of the alkoxysilane;

b) depositing the composition onto a semiconductor substrate while evaporating at least a portion of the relatively high volatility solvent composition;

c) exposing the composition to a water vapor and a base vapor; and d) evaporating the relatively low volatility solvent composition, thereby forming a relatively high porosity, low dielectric constant, silicon containing polymer composition on the semiconductor substrate.

It has now been found that by the use of the above $C_1$ to $C_4$ alkylether of a $C_1$ to $C_4$ alkylene glycol in the precursor composition, that an unexpectedly stable precursor composition can be formed.

DETAILED DESCRIPTION OF THE PREFERRED EMBODIMENT

Figure 1:
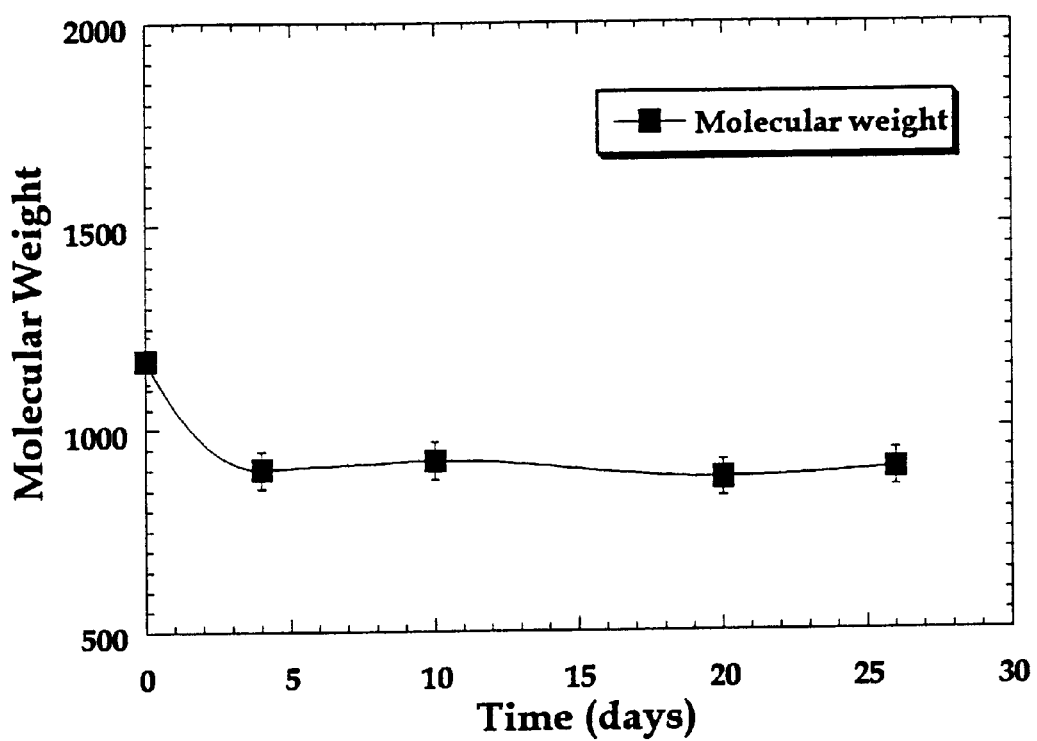
FIG. 1 is a graph of the change in molecular weight as a function of time for a ethanol-diluted ethylene glycol precursor.

The invention forms a blend of at least one alkoxysilane with a relatively high volatility solvent composition, a relatively low volatility solvent composition, optional water and an optional catalytic amount of an acid. Water is included to provide a medium for hydrolyzing the alkoxysilane. This blend is then applied onto a substrate. The high volatility solvent evaporates during and immediately after deposition of the mixture. The low volatility solvent is then removed by increasing the temperature.

Useful alkoxysilanes for this invention include those which have the formula:

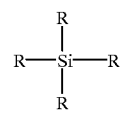

wherein at least 2 of the R groups are independently $C_1$ to $C_4$ alkoxy groups and the balance, if any, are independently selected from the group consisting of hydrogen, alkyl, phenyl, halogen, substituted phenyl. For purposes of this invention, the term alkoxy includes any other organic group which can be readily cleaved from silicon at temperatures near room temperature by hydrolysis. R groups can be ethylene glycoxy or propylene glycoxy or the like, but preferably all four R groups are methoxy, ethoxy, propoxy or butoxy. The most preferred alkoxysilanes nonexclusively include tetraethoxysilane (TEOS) and tetramethoxysilane.

The relatively high volatility solvent composition is one which evaporates at a temperature below, and preferably significantly below that of the relatively low volatility solvent composition. The relatively high volatility solvent composition preferably has a boiling point of about 120° C. or less, more preferably about 100° C. or less. Suitable high volatility solvent composition nonexclusively include methanol, ethanol, n-propanol, isopropanol, n-butanol and mixtures thereof Other relatively high volatility solvent compositions which are compatible with the other ingredients can be readily determined by those skilled in the art.

The relatively low volatility solvent composition is one which evaporates at a temperature above, preferably significantly above that of the relatively high volatility solvent composition. The relatively low volatility solvent composition preferably has a boiling point of about 175° C. or more, more preferably about 200° C. or more. Suitable low volatility solvent compositions nonexclusively include a $C_1$ to $C_4$ alkylether of a $C_1$ to $C_4$ alkylene glycol which is miscible in water and alkoxysilanes, having a hydroxyl concentration of 0.0084 mole/cm³ or less, with a boiling point of about 175° C. or more at atmospheric pressure and a weight average molecular weight of about 120 or more.

Such preferably have the formula $R_1(OR_2)_n OH$ wherein $R_1$ is a linear or branched $C_1$ to $C_4$ alkyl group, $R_2$ is a $C_1$ to $C_4$ alkylene group, and n is 2–4. Preferred low volatility solvent composition components include di(ethylene)glycol monomethyl ether, tri(ethylene)glycol monomethyl ether, tetra(ethylene)glycol monomethyl ether; di(propylene) glycol monomethyl ether, tri(propylene)glycol monomethyl ether and mixtures thereof Their properties are as follows. Boiling points are at atmospheric pressure.

impurities, preferably no more than about 50 parts per billion and more preferably no more than about 10 parts per billion of trace metal impurities. Such may be obtained by any convenient means such as by filtration, distillation or vacuum distillation.

The optional acid serves to catalyze the reaction of the alkoxysilane with the relatively high volatility solvent composition, a relatively low volatility solvent composition and water. Suitable acids are nitric acid and compatible organic acids which are volatile, i.e. which evaporate from the resulting reaction product under the process operating conditions, and which do not introduce impurities into the reaction product.

The alkoxysilane component is present in an amount of from about 3% to about 50% by weight of the overall blend. A more preferred range is from about 5% to about 45% and most preferably from about 10% to about 40%.

The high volatility solvent composition component is present in an amount of from about 20% to about 90% by weight of the overall blend. A more preferred range is from about 30% to about 70% and most preferably from about 40% to about 60%.

The low volatility solvent composition component is present in an amount of from about 1 to about 40% by weight of the overall blend. A more preferred range is from about 3% to about 30% and most preferably from about 5% to about 20%.

The mole ratio of water to silane is preferably from about 0 to about 50. A more preferred range is from about 0.1 to about 10 and most preferably from about 0.5 to about 1.5.

The acid is present in a catalytic amount which can be readily determined by those skilled in the art. Preferably the molar ratio of acid to silane ranges from about 0 to about 0.2, more preferably from about 0.001 to about 0.05, and most preferably from about 0.005 to about 0.02.

The alkoxysilane containing composition is then coated on a substrate optionally having a pattern of lines on its

| Compound | Formula | Boiling Point ° C. | Molecular Weight | Hydroxyl Concentration (mole/cm³) |
|---|---|---|---|---|
| di(ethylene) glycol monomethyl ether | $CH_3(OCH_2CH_2)_2OH$ | 194 | 120.1 | 0.0084 |
| tri(ethylene) glycol monomethyl ether | $CH_3(OCH_2CH_2)_3OH$ | 260 | 164.2 | 0.0062 |
| tetra(ethylene) glycol monomethyl ether | $CH_3(OCH_2CH_2)_4OH$ | 302 | 208.2 | 0.0048 |
| di(propylene) glycol monomethyl ether | $CH_3(OCH_2CH_2CH_2)_2OH$ | 218 | 148.2 | 0.0063 |
| tri(propylene) glycol monomethyl ether | $CH_3(OCH_2CH_2CH_2)_3OH$ | 267 | 190.3 | 0.0049 |

It has further been found that the high and low volatility solvent compositions as well as the alkoxysilane should be ultrapurified prior to blending them together. When they are ultrapurified it has been found that the amount of trace metals in the resulting nanoporous layer is significantly reduced. This results in a reduction of layer interference such as RC delay, power consumption and crosstalk in the integrated circuits produced with these materials.

Within the context of the present invention, the term ultrapurified means that the solvent compositions should have no more than about 250 parts per billion of trace metal surface, and forms a dielectric film on the surface. Typical substrates are those suitable to be processed into an integrated circuit or other microelectronic device. Suitable substrates for the present invention non-exclusively include semiconductor materials such as gallium arsenide (GaAs), silicon and compositions containing silicon such as crystalline silicon, polysilicon, amorphous silicon, epitaxial silicon, and silicon dioxide ($SiO_2$) and mixtures thereof The layer is relatively uniformly applied to the substrate. The lines, when present, are lithographically formed and may be composed of a metal, an oxide, a nitride or an oxynitride.

Suitable materials include silica, silicon nitride, titanium nitride, tantalum nitride, aluminum, aluminum alloys, copper, copper alloys, tantalum, tungsten and silicon oxynitride. These lines form the conductors or insulators of an integrated circuit. Such are typically closely separated from one another at distances of about 20 micrometers or less, preferably 1 micrometer or less, and more preferably from about 0.05 to about 1 micrometer.

After deposition, the high volatility solvent is then partially evaporated over a period of seconds or minutes. At this point, the film is a viscous liquid of the silica precursors and the less volatile solvent. Slightly elevated temperatures may optionally be employed to accelerate this step. Such temperatures may range from about 20° C. to about 80° C., preferably range from about 20° C. to about 50° C. and more range from about 20° C. to about 35° C.

Then the coating is exposed to both a water vapor and a base vapor. The base vapor may be introduced first followed by the water vapor, or both the water vapor and the base vapor may be introduced simultaneously. Water can be provided by ambient air containing moisture. The water vapor causes a continued hydrolysis of the alkoxysilane alkoxy groups, and the base catalyzes condensation of the hydrolyzed alkoxysilane and serves to increase molecular weight until the coating gels and ultimately increases gel strength.

If the condensation rate is much faster than hydrolysis, a significant number of alkoxy groups will remain after the gel point. If little hydrolysis has occurred, then the film will maintain the same thickness as after the coating step. Continued exposure to basic water vapor results in continued hydrolysis of alkoxy groups forming silanols and the generation of volatile alcohols. The film is then dried in a conventional way by solvent evaporation of the less volatile solvent with no further shrinkage. Elevated temperatures may be employed to dry the coating in this step. Such temperatures may range from about 20° C. to about 450° C., preferably from about 50° C. to about 350° C. and more preferably from about 175° C. to about 320° C. The silicon containing polymer composition preferably has a dielectric constant of from about 1.3 to about 3.5, more preferably from about 1.5 to about 3.0, and most preferably from about 1.8 to about 2.5. The pore size of silica composition ranges from about 1 nm to about 100 nm, more preferably from about 2 nm to about 30 nm, and most preferably from about 3 nm to about 20 nm. The density of the silicon containing composition, including the pores, ranges from about 0.25 to about 1.9 g/cm$^2$, more preferably from about 0.4 to about 1.6 g/cm$^2$, and most preferably from about 0.7 to about 1.2 g/cm$^2$.

Suitable bases for use in the base vapor nonexclusively include ammonia and amines, such as primary, secondary and tertiary alkyl amines, aryl amines, alcohol amines and mixtures thereof which have a boiling point of about 200° C. or less, preferably 100° C. or less and more preferably 25° C. or less. Preferred amines are methyl amine, dimethyl amine, trimethyl amine, n-butyl amine, n-propyl amine, tetramethyl ammonium hydroxide, piperidine and 2-methoxyethyl amine. The ability of an amine to accept a proton in water is measured in terms of the basicity constant $K_b$, and $pK_b = -\log K_b$. In the preferred embodiment, the $pK_b$ of the base may range from about less than 0 to about 9. A more preferred range is from about 2 to about 6 and most preferably from about 4 to about 5.

In the preferred embodiment, the mole ratio of water vapor to base vapor ranges from about 1:3 to about 1:00, preferably from about 1:5 to about 1:50, and more preferably from about 1:10 to about 1:30.

The following non-limiting examples serve to illustrate the invention.

EXAMPLE 1 (COMPARATIVE)

This example illustrates that a tetraethylene glycol (TEG) based precursor has a less stable shelf-life when diluted with EtOH than triethylene glycol monomethyl ether. During synthesis, TEG undergoes some crosslinking in the polymer and the molecular weight increases. When the precursor is diluted to achieve the correct solids content for adequate deposition, the polymer de-polymerizes making it slightly unstable.

A precursor was synthesized by adding 61.0 mL of tetraethoxysilane, 61.0 mL of tetraethylene glycol, 4.87 mL of deionized water, and 0.2 mL of 1N nitric acid together in a round bottom flask. The solution was allowed to mix vigorously then heated to ~80° C. and refluxed for 1.5 hours to form a solution. After the solution was allowed to cool, it was stored in refrigeration at 4° C.

Molecular weight measurements were performed to track the stability of the precursor by gel permeation chromatography (GPC) after the solution was diluted with ethanol to a 50% by weight amount and 0.3% by weight with FC-430 surfactant (3M, St. Paul Minn. 55144). The solution is filtered to 0.2 μm with a teflon filter and diluted with tetrahydrofuran at a 0.15:1 (solution/tetrahydrofuran) volume ratio. Multiple samples (3) were run to confirm the reproducibility of the instrument. The average molecular weight was plotted as a function of time (in days) as seen in FIG. 1 and Table 1. The molecular weight drops by 18% but after 4 days appears to have stabilized.

TABLE 1

Change in molecular weight as a function of time for a ethanol diluted tetraethylene glycol precursor

| Time (days) | Average Molecular weight |
|---|---|
| 0 | 1172 |
| 4 | 901 |
| 10 | 921 |
| 20 | 878 |
| 26 | 900 |

EXAMPLE 2

This example illustrates that triethylene glycol monomethyl ether (TriEGMME) has a stable shelf-life when diluted with EtOH. During synthesis, TriEGMME does not undergo crosslinking so the polymer does not de-polymerize.

A precursor was synthesized by adding 94.0 mL of tetraethoxysilane, 61.0 mL of TriEGMME, 7.28 mL of deionized water, and 0.31 mL of 1N nitric acid together in a round bottom flask. The solution was allowed to mix vigorously then heated to ~80° C. and refluxed for 1.5 hours to form a solution. After the solution was allowed to cool, it was stored in refrigeration at 4° C.

Molecular weight measurements were performed to track the stability of the precursor by gel permeation chromatography (GPC) after the solution was diluted with ethanol to a 30% by weight amount. The solution is filtered to 0.2 $\mu$m with a teflon filter and diluted with tetrahydrofuran at a 0.15:1 (solution/tetrahydrofuran) volume ratio.

Figure 2:
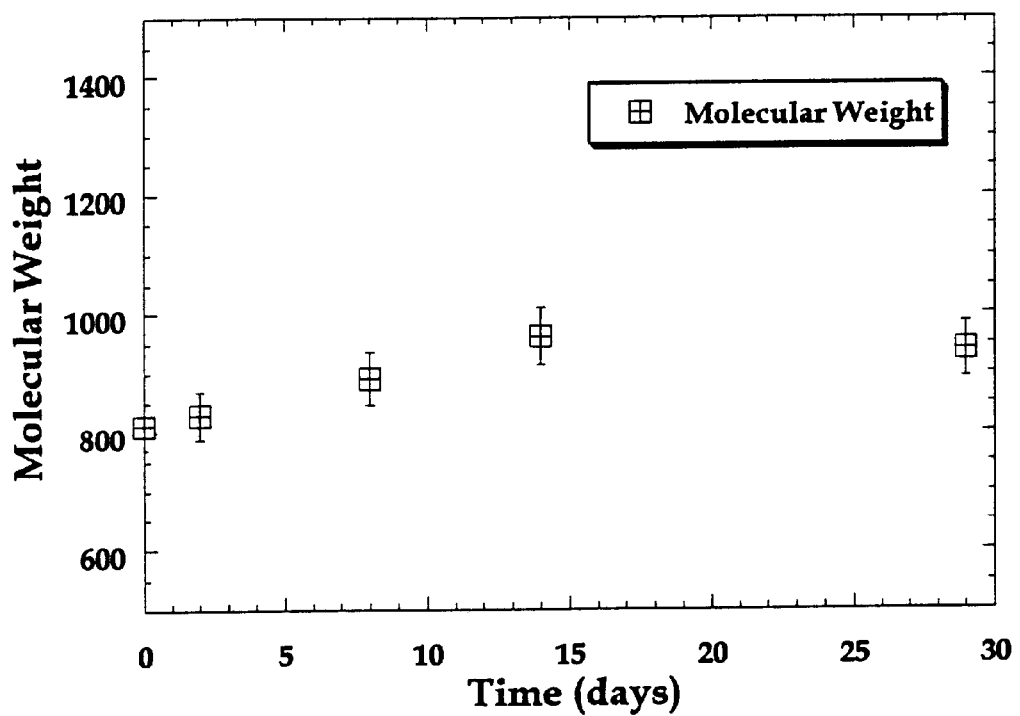
FIG. 2 is a graph of the change in molecular weight as a function of time for a ethanol diluted triethylene glycol monomethyl ether precursor.

Multiple samples (3) were run to confirm the reproducibility of the instrument. The average molecular weight was plotted as a function of time (in days) as seen in FIG. 2 and Table 2. The molecular weight does not indicate any sign of de-polymerization and the stability is quite good within the error of the instrument.

TABLE 2

Change in molecular weight as a function of time for a ethanol diluted triethyleneglycol monomethyl ether

| Time (days) | Average Molecular weight |
|---|---|
| 0 | 811 |
| 2 | 829 |
| 8 | 891 |
| 14 | 962 |
| 29 | 939 |
| 56 | 1020 |

EXAMPLE 3 (COMPARATIVE)

This example illustrates that tetraethylene glycol (TEG) precursors yield poor film appearance when inspected by scanning electron microscopy.

A precursor was synthesized by adding 61. 0 mL of tetraethoxysilane, 61.0 mL of tetraethylene glycol, 4.87 mL of deionized water, and 0.2 mL of 1N nitric acid together in a round bottom flask. The solution was allowed to mix vigorously then heated to ~80° C. and refluxed for 1.5 hours to form a solution. After the solution was allowed to cool, it was diluted 50% by weight with ethanol to reduce the viscosity and 0.3% by weight with FC-430 surfactant (3M St. Paul Minn. 55144). The diluted precursor was filtered to 0.1 $\mu$m using a teflon filter. Approximately 2.0 ml of the precursor was deposited onto a 4" inch silicon wafer on a spin chuck, and spun at 2500 rpm for 30 seconds.

The films were gelled and aged in a vacuum chamber using the following conditions. The chamber was evacuated to 250 torr. Next, 15M ammonium hydroxide was heated and equilibrated at 45° C. and dosed into the chamber to increase the pressure to 660 torr for 2–3 minutes. Finally, chamber was then evacuated to 250 torr and backfilled with nitrogen.

The films were then solvent exchanged by which 20–30 mL of a 50/50 (by vol.) mixture of acetone and hexamethyldisilazane were spun on the film at 250 rpm for 20 seconds without allowing the film to dry. The films were then spun dry at 1000 rpm for 5 seconds. The film was heated at elevated temperatures for 1 min. each at 175° C. and 320° C. in air. The film was then inspected by scanning electron microscopy (SEM) to view any defects in the microstructure. The SEM image clearly demonstrates that the film has holes throughout the cross-section.

EXAMPLE 4

This example illustrates that triethylene glycol monomethyl ether (TriEGMME) precursors yield excellent film appearance when inspected by scanning electron microscopy.

A precursor was synthesized by adding 94.0 mL of tetraethoxysilane, 61.0 mL of triethylene glycol monomethyl ether, 7.28 mL of deionized water, and 0.31 mL of 1N nitric acid together in a round bottom flask. The solution was allowed to mix vigorously then heated to ~80° C. and refluxed for 1.5 hours to form a stock solution. After the solution was allowed to cool, it was diluted 30% by weight with ethanol to reduce the viscosity. The diluted precursor was filtered to 0.1 $\mu$m using a teflon filter. Approximately 2.0 ml of the precursor was deposited onto a 4" inch silicon wafer on a spin chuck, and spun at 2500 rpm for 30 seconds. The films were gelled and aged in a vacuum chamber using the following conditions. The chamber was evacuated to 250 torr. Next, 15M ammonium hydroxide was heated and equilibrated at 45° C. and dosed into the chamber to increase the pressure to 660 torr for 2–3 minutes. Finally, chamber was then evacuated to 250 torr and backfilled with nitrogen. The films were then solvent exchanged by which 20–30 mL of a 50/50 (by vol.) mixture of acetone and hexamethyldisilazane were spun on the film at 250 rpm for 20 seconds without allowing the film to dry. The films were then spun dry at 1000 rpm for 5 seconds. The film was heated at elevated temperatures for 1 min. each at 175° C. and 320° C. in air. The film was then inspected by scanning electron microscopy (SEM) to view any defects in the microstructure. An SEM image and clearly shows excellent microstructure with no gross defects:

EXAMPLE 5 (COMPARATIVE)

Figure 3:
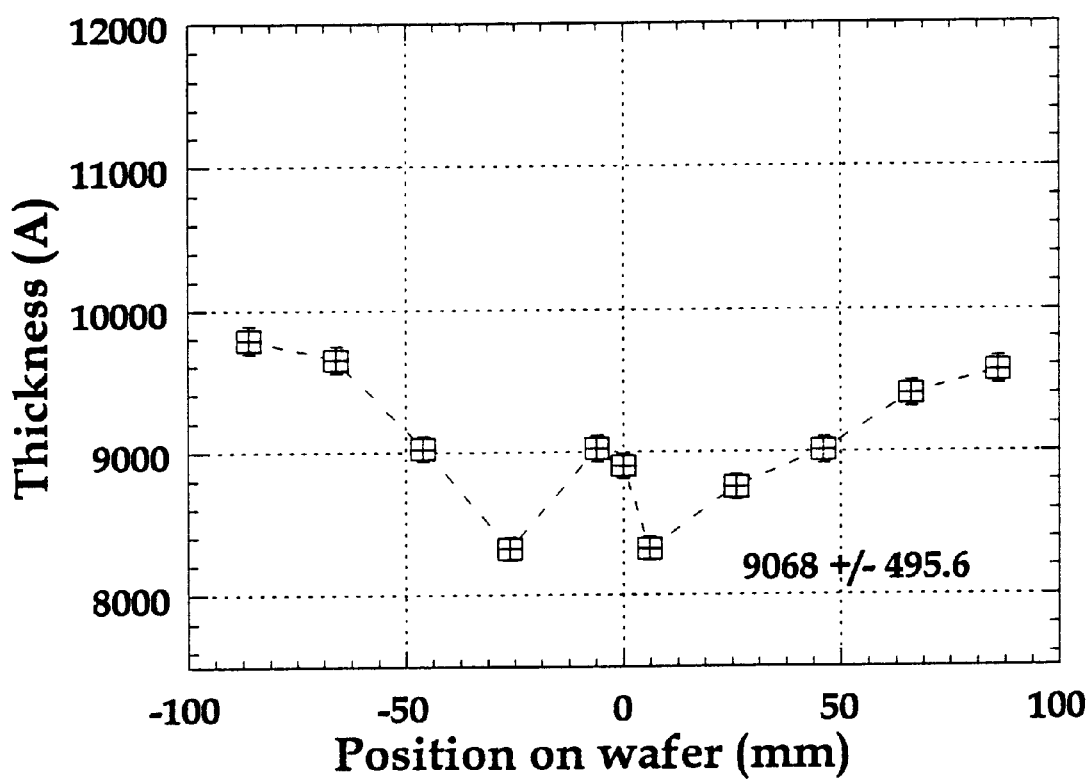
FIG. 3 is a graph of thickness uniformity across a 200 mm wafer prepared from tetraethylene glycol.

This example illustrates that tetraethylene glycol (TEG) precursors yield poor film uniformity across a 8" wafer when measured by ellipsometry. The precursor was synthesized by adding 61.0 mL of tetraethoxysilane, 61.0 mL of tetraethylene glycol, 4.87 mL of deionized water, and 0.2 mL of 1N nitric acid together in a round bottom flask. The solution was allowed to mix vigorously then heated to ~80° C. and refluxed for 1.5 hours to form a solution. After the solution was allowed to cool, it was diluted 50% by weight with ethanol to reduce the viscosity and 0.3% by weight with FC430 surfactant (3M, St. Paul Minn. 55144). The diluted precursor was filtered to 0.1 $\mu$m using a teflon filter. Approximately 2.0 ml of the precursor was deposited onto a 8" inch silicon wafer on a spin chuck, and spun at 2500 rpm for 30 seconds. The films were gelled and aged in a vacuum chamber using the following conditions. The chamber was evacuated to 250 torr. Next, 15M ammonium hydroxide (Aldrich Chemical Company, Milwaukee, Wis. 53201) was heated and equilibrated at 45° C. and dosed into the chamber to increase the pressure to 660 torr for 2–3 minutes. Finally, chamber was then evacuated to 250 torr and backfilled with nitrogen. The films were then solvent exchanged by which 20–30 mL of a 50/50 (by vol.) mixture of acetone and hexamethyldisilazane were spun on the film at 250 rpm for 20 seconds without allowing the film to dry. The films were then spun dry at 1000 rpm for 5 seconds. The film was heated at elevated temperatures for 1 min. each at 175° C. and 320° C. in air. The film was then inspected by single wavelength multiple angle ellipsometry to determine the refractive index and thickness across a wafer as seen in FIG. 3 and Table 3.

TABLE 3

Thickness uniformity across a 200 mm wafer.

| Position on wafer (every 20 mm) | Thickness (Angstroms) |
|---|---|
| −86 | 9787 |
| −66 | 9650 |
| −46 | 9023 |
| −26 | 8325 |
| −6 | 8700 |
| 14 | 8300 |
| 6 | 8525 |
| 26 | 8830 |
| 46 | 9007 |
| 66 | 9451 |
| 86 | 9566 |

EXAMPLE 6

This example illustrates that triethylene glycol monomethyl ether (TriEGMME) precursors yield excellent film uniformity when inspected by ellipsometry.

The precursor was synthesized by adding 94.0 mL of tetraethoxysilane, 61.0 mL of triethylene glycol monomethyl ether, 7.28 mL of deionized water, and 0.31 mL of 1N nitric acid together in a round bottom flask. The solution was allowed to mix vigorously then heated to ~80° C. and refluxed for 1.5 hours to form a stock solution. After the solution was allowed to cool, it was diluted 50% by weight with ethanol to reduce the viscosity. The diluted precursor was filtered to 0.1 µm using a teflon filter. Approximately 2.0 ml of the precursor was deposited onto a 4 inch silicon wafer on a spin chuck, and spun at 2500 rpm for 30 seconds. The films were gelled and aged in a vacuum chamber using the following conditions. The chamber was evacuated to 250 torr. Next, 15M ammonium hydroxide was heated and equilibrated at 45° C. and dosed into the chamber to increase the pressure to 660 torr for 2–3 minutes. Finally, chamber was then evacuated to 250 torr and backfilled with nitrogen.

Figure 4:
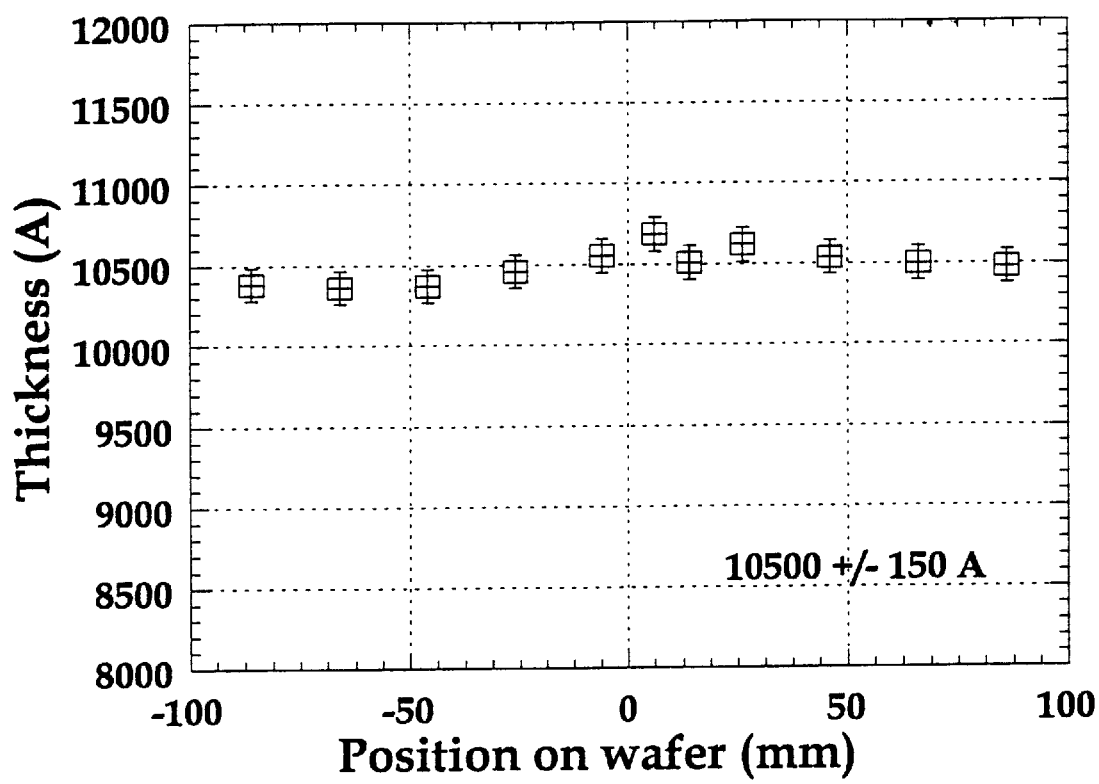
FIG. 4 is a graph of thickness uniformity across a 200 mm wafer prepared from triethylene glycol monomethyl ether.

The films were then solvent exchanged by which 20–30 mL of a 50/50 (by vol.) mixture of acetone and hexamethyldisilazane were spun on the film at 250 rpm for 20 seconds without allowing the film to dry. The films were then spun dry at 1000 rpm for 5 seconds. The film was heated at temperatures for 1 min. each at 175° C. and 320° C. in air. The film was then inspected by single wavelength multiple angle ellipsometry to determine the refractive index and thickness across a wafer as seen in FIG. 4 and Table 4.

TABLE 4

Thickness uniformity across a 200 mm wafer.

| Position on wafer (every 20 mm) | Thickness (Angstroms) |
|---|---|
| −86 | 10622 |
| −66 | 10567 |
| −46 | 10546 |
| −26 | 10520 |
| −6 | 10488 |
| 14 | 10528 |
| 6 | 10577 |
| 26 | 10558 |
| 46 | 10578 |
| 66 | 10624 |
| 86 | 10647 |

EXAMPLE 7

This example illustrates that the metals content for a nanoporous silica film derived from a triethylene glycol monomethyl ether precursor, can be significantly lowered when the raw materials of the precursor are distilled prior to synthesis.

The raw materials were distilled by one of two methods based on their boiling points and hydrolytic stability. Ethanol was distilled by using a simple distillation apparatus. The ethanol was added to a flask and heated to its boiling point. The distillation occurred by allowing the vapors to rise up a cooled condenser. After a few minutes the vapors became saturated and condensed, and were collected in a receiver flask. The ethanol was decanted and stored in a polypropylene bottle.

Tetraethoxysilane (TEOS) and triethylene glycol monomethyl ether (TriEGMME) were vacuum distilled due to TEOS being a readily hydrolyzable material and TriEGMME having a high boiling point. The solvent was added to a two neck flask that was connected to a thermometer and a Friedrich condenser that is jacketed and flowing cooled water throughout it. The vacuum source was connected to the system and the other end of the condenser was connected to the distillate flask. For distillation of TEOS, the sample was heated by connecting the heating mantle to a variac which was set at 30 volts. A vacuum of 15–20 torr was applied to the apparatus and the purified TEOS vapors condensed and dripped into the distillate flask. This distillate of TEOS was then decanted into and stored in a polypropylene bottle at room temperature. For distillation of TriEGMME, the variac was set at 40 volts and a vacuum of 15–20 torr was drawn on the apparatus. The solvent was purified and the distillate was decanted and stored in a polypropylene bottle at room temperature.

The precursor was synthesized by adding 61.0 mL of TEOS, 61.0 mL of TriEGMME, 4.87 mL of deionized water, and 0.2 mL of 1N nitric acid together in a round bottom flask. The solution was allowed to mix vigorously then heated to ~80° C. and refluxed for 1.5 hours to form a solution. After the solution was allowed to cool, it was diluted 30% by weight with ethanol to reduce the viscosity. The diluted precursor was filtered to 0.1 µm using a teflon filter. A sample of the precursor was analyzed for trace metals. A second precursor was synthesized in the above matter, in which none of the raw materials were distilled for comparative purposes. The results are shown in Table 5 in parts per billion (ppb) units.

TABLE 5

Units in (ppb)

| Metal | Detection Limit (D.L.) | Precursor 1 (raw materials not distilled) | Precursor 1 (raw materials distilled) |
|---|---|---|---|
| Al | 0.05 | 0.17 | 0.082 |
| Sb | 0.05 | <0.05 | <0.05 |
| As | 0.1 | 0.11 | <0.1 |
| Ba | 0.01 | 0.5 | <0.01 |
| Be | 0.05 | <0.05 | <0.05 |
| Bi | 0.05 | <0.05 | <0.05 |
| B | 0.1 | 45 | 2.2 |
| Cd | 0.01 | 0.1 | <0.01 |
| Ca | 0.1 | 0.18 | <0.1 |
| Cr | 0.05 | 2.3 | <0.05 |
| Co | 0.01 | 0.028 | 0.012 |
| Cu | 0.05 | 2.1 | 0.055 |
| Ga | 0.01 | 0.019 | <0.01 |
| Ge | 0.05 | <0.05 | <0.05 |
| Fe | 0.1 | 40 | 0.23 |
| Pb | 0.05 | 3.0 | <0.05 |
| Li | 0.05 | <0.05 | <0.05 |
| Mg | 0.05 | 2.9 | 0.42 |
| Mn | 0.05 | 0.62 | <0.05 |
| Mo | 0.05 | 0.33 | <0.05 |
| Ni | 0.05 | 1.2 | <0.05 |
| K | 0.1 | 25 | 0.75 |
| Ag | 0.05 | <0.05 | <0.05 |
| Na | 0.1 | 1090 | 2.2 |
| Sr | 0.01 | 0.06 | <0.01 |
| Sn | 0.05 | 0.67 | <0.05 |
| Ti | 0.05 | 0.082 | <0.05 |
| V | 0.05 | <0.05 | <0.05 |
| Zn | 0.05 | 385 | 0.32 |
| Zr | 0.01 | 0.023 | <0.01 |

In all cases the precursor that had the raw materials distilled yielded substantially lower metals levels than the non-distilled case. Approximately 8–10 ml of the precursors that were distilled were deposited onto 8" inch silicon wafers on a spin chuck, and spun at 2500 rpm for 30 seconds. The films were gelled and aged in a vacuum chamber using the following conditions. The chamber was evacuated to 250 torr. Next, 15M ammonium hydroxide was heated and equilibrated at 45° C. and dosed into the chamber to increase the pressure to 660 torr for 2–3 minutes. Finally, chamber was evacuated to 250 torr and backfilled with nitrogen. The film was heated at elevated temperatures for 1 min. each at 175° C. and 320° C. in air. Films were analyzed for trace metals by either ICP-MS or GFAAS. A blank control where no precursor was deposited onto the substrate was sent to determine the contribution of metals from the silicon substrate. Table 6 shows the results of the metals analysis.

TABLE 6

(Units in E10 atoms/cm$^2$)

| Metal | Detection Limit (D.L.) | Control (blank no film) | Film 1 (raw materials not distilled) | Film 2 (raw materials distilled) |
|---|---|---|---|---|
| Al | 0.05 | 75 | 148 | 60 |
| Sb | 0.05 | 0.008 | <0.05 | .007 |
| As | 0.1 | 0.14 | <0.05 | <0.05 |
| Ba | 0.01 | 0.015 | 0.009 | 0.033 |
| Be | 0.05 | <0.5 | <0.5 | <0.5 |
| Bi | 0.05 | <0.0 | 0.080 | <0.05 |
| B | 0.1 | 104 | 192 | 200 |
| Cd | 0.01 | 0.08 | 0.04 | 0.04 |
| Ca | 0.1 | 7 | 11 | 16 |
| Cr | 0.05 | 0.1 | 1.5 | 0.3 |
| Co | 0.01 | <0.02 | <0.02 | 0.05 |
| Cu | 0.05 | 0.2 | 0.7 | 0.1 |
| Ga | 0.01 | <0.02 | 0.16 | <0.02 |
| Ge | 0.05 | <0.02 | <0.02 | <0.02 |
| Fe | 0.1 | <0.3 | 6.2 | 1.2 |
| Pb | 0.05 | 0.19 | 0.081 | 0.15 |
| Li | 0.05 | 1.1 | 0.2 | <0.05 |
| Mg | 0.05 | 2.4 | 26 | 2.6 |
| Mn | 0.05 | 0.013 | 0.15 | 0.017 |
| Mo | 0.05 | 0.07 | 0.09 | <0.05 |
| Ni | 0.05 | 0.09 | 0.85 | <0.05 |
| K | 0.1 | <0.1 | 16 | <0.1 |
| Ag | 0.05 | <0.05 | <0.05 | <0.05 |
| Na | 0.1 | 1.5 | 1090 | 1.5 |
| Sr | 0.01 | 0.036 | 0.006 | 0.030 |
| Sn | 0.05 | 0.8 | 0.2 | 0.0 |
| Ti | 0.05 | 0.3 | 0.9 | <0.2 |
| V | 0.05 | <0.05 | 0.11 | <0.05 |
| Zn | 0.05 | 4.4 | 10 | 0.6 |
| Zr | 0.01 | 0.12 | 0.075 | <0.01 |

The results show that distilling the raw materials of the precursor lead to a lower metal aerial density. In particular, the levels of sodium and potassium are decreased substantially. Boron and Aluminum showed higher levels in all samples including the control.

What is claimed is:

1. A nanoporous silica precursor composition which comprises at least one alkoxysilane; at least one relatively low volatility solvent composition comprising a linear or branched $C_1$ to $C_4$ alkyl ether of a $C_1$ to $C_4$ alkylene glycol which is miscible in water and alkoxysilanes, having a hydroxyl concentration of 0.0084 mole/cm$^3$ or less, a boiling point of about 175° C. or more at atmospheric pressure and a weight average molecular weight of about 120 or more; at least one relatively high volatility solvent composition having a boiling point below that of the relatively low volatility solvent composition; optional water and an optional catalytic amount of an acid.

2. The composition of claim 1 which comprises water.

3. An article which comprises a substrate and the composition of claim 2 on the substrate.

4. The composition of claim 1 which comprises a catalytic amount of an acid.

5. An article which comprises a substrate and the composition of claim 4 on the substrate.

6. The composition of claim 1 which comprises both water and a catalytic amount of an acid.

7. An article which comprises a substrate and the composition of claim 6 on the substrate.

8. The composition of claim 1 which is absent of water and an acid catalyst.

9. An article which comprises a substrate and the composition of claim 8 on the substrate.

10. The composition of claim 1 wherein the alkoxysilane comprises one or more components selected from the group consisting of alkoxysilanes having the formula:

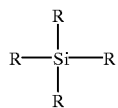

wherein at least 2 of the R groups are independently $C_1$ to $C_4$ alkoxy groups and the balance, if any, are independently selected from the group consisting of hydrogen, alkyl, phenyl, halogen, substituted phenyl.

11. The composition of claim 10 wherein each R is methoxy, ethoxy or propoxy.

12. An article which comprises a substrate and the composition of claim 11 on the substrate.

13. An article which comprises a substrate and the composition of claim 10 on the substrate.

14. The composition of claim 1 wherein the alkoxysilane comprises one or more components selected from the group consisting of tetraethoxysilane and tetramethoxysilane.

15. An article which comprises a substrate and the composition of claim 14 on the substrate.

16. The composition of claim 1 wherein the relatively high volatility solvent composition has a boiling point of about 120° C. or less.

17. An article which comprises a substrate and the composition of claim 16 on the substrate.

18. The composition of claim 1 wherein the relatively high volatility solvent composition comprises one or more components selected form the group consisting of methanol, ethanol, n-propanol, isopropanol, n-butanol and mixtures thereof.

19. An article which comprises a substrate and the composition of claim 18 on the substrate.

20. The composition of claim 1 wherein the relatively low volatility solvent composition comprises di(ethylene)glycol monomethyl ether, tri(ethylene)glycol monomethyl ether, tetra(ethylene)glycol monomethyl ether; di(propylene) glycol monomethyl ether, tri(propylene)glycol monomethyl ether and mixtures thereof.

21. An article which comprises a substrate and the composition of claim 20 on the substrate.

22. The composition of claim 1 wherein the precursor composition has no more than about 250 parts per billion of trace metal impurities.

23. An article which comprises a substrate and the composition of claim 22 on the substrate.

24. An article which comprises a substrate and the composition of claim 1 on the substrate.

25. A process for forming a nanoporous dielectric coating on a substrate which comprises
 a) blending a nanoporous silica precursor composition which comprises at least one alkoxysilane; at least one relatively low volatility solvent composition comprising a linear or branched $C_1$ to $C_4$ alkyl ether of a $C_1$ to $C_4$ alkylene glycol which is miscible in water and alkoxysilanes, having a hydroxyl concentration of 0.0084 mole/cm$^3$ or less, a boiling point of about 175° C. or more at atmospheric pressure and a weight average molecular weight of about 120 or more; at least one relatively high volatility solvent composition having a boiling point below that of the relatively low volatility solvent composition; optional water and an optional catalytic amount of an acid, thus forming a mixture and causing a partial hydrolysis and partial condensation of the alkoxysilane;
 b) depositing the composition onto a substrate while evaporating at least a portion of the relatively high volatility solvent composition;
 c) exposing the composition to a water vapor and a base vapor; and
 d) evaporating the relatively low volatility solvent composition, thereby forming a relatively high porosity, low dielectric constant, silicon containing polymer composition on the substrate.

26. The process of claim 25 wherein step (a) comprises blending water in the composition.

27. The process of claim 25 wherein step (a) further comprises blending a catalytic amount of an acid in the composition.

28. The process of claim 25 wherein the alkoxysilane comprises one or more components selected from the group consisting of alkoxysilanes having the formula:

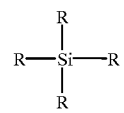

wherein at least 2 of the R groups are independently $C_1$ to $C_4$ alkoxy groups and the balance, if any, are independently selected from the group consisting of hydrogen, alkyl, phenyl, halogen, substituted phenyl.

29. The process of claim 28 wherein each R is methoxy, ethoxy or propoxy.

30. The process of claim 25 wherein the alkoxysilane comprises one or more components selected from the group consisting of tetraethoxysilane and tetramethoxysilane.

31. The process of claim 25 wherein the relatively high volatility solvent composition has a boiling point of about 120° C. or less.

32. The process of claim 25 wherein the relatively high volatility solvent composition comprises one or more components selected form the group consisting of methanol, ethanol, n-propanol, isopropanol, n-butanol and mixtures thereof.

33. The process of claim 25 wherein the relatively low volatility solvent composition comprises di(ethylene)glycol monomethyl ether, tri(ethylene)glycol monomethyl ether, tetra(ethylene)glycol monomethyl ether; di(propylene) glycol monomethyl ether, tri(propylene)glycol monomethyl ether and mixtures thereof.

34. The process of claim 25 wherein the base vapor comprises one or more components selected from the group consisting of ammonia, amines and mixtures thereof.

35. The process of claim 25 wherein the mole ratio of water vapor to base vapor ranges from about 1:3 to about 1:100.

36. The process of claim 25 wherein the base vapor has a $pK_b$ of from about less than 0 to about 9.

37. The process of claim 25 wherein the substrate comprises raised pattern of lines comprising a metal, an oxide, a nitride and/or an oxynitride material.

38. The process of claim 25 wherein the substrate comprises a semiconductor material.

39. The process of claim 25 wherein the substrate comprises silicon or gallium arsenide.

40. The process of claim 25 wherein the mole ratio of water vapor to base vapor ranges from about 1:3 to about 1:100.

41. The process of claim 25 wherein the precursor composition has no more than about 250 parts per billion of trace metal impurities.

* * * * *